United States Patent [19]

Umezawa et al.

[11] 4,240,975

[45] Dec. 23, 1980

[54] BESTATIN

[75] Inventors: Hamao Umezawa, Tokyo; Takaaki Aoyagi, Fujisawa; Tomohisa Takita, Asaka; Rinzo Nishizawa; Tetsushi Saino, both of Tokyo, all of Japan

[73] Assignee: Zaidan Hojin Biseibutsu Kagaku Kenkyu Kai, Tokyo, Japan

[21] Appl. No.: 79,777

[22] Filed: Sep. 26, 1979

Related U.S. Application Data

[60] Continuation of Ser. No. 868,571, Jan. 10, 1978, abandoned, which is a division of Ser. No. 809,835, Jun. 24, 1977, Pat. No. 4,189,604, which is a continuation-in-part of Ser. No. 800,820, May 26, 1977, abandoned, which is a continuation-in-part of Ser. No. 703,863, Jul. 9, 1976, abandoned.

[30] Foreign Application Priority Data

Jul. 21, 1976 [JP] Japan ................................ 51-85992

[51] Int. Cl.$^3$ ...................... C07C 69/96; C07C 101/72
[52] U.S. Cl. ........................................ 260/463; 560/29; 560/22; 562/437; 562/444; 562/452
[58] Field of Search .................... 560/22, 29; 562/444, 562/437, 452; 260/463

[56] References Cited

U.S. PATENT DOCUMENTS

| | | | |
|---|---|---|---|
| 3,255,202 | 6/1966 | Johnson | 560/39 |
| 3,852,338 | 12/1974 | Kaiser et al. | 560/29 |
| 3,859,331 | 1/1975 | Kaiser et al. | 260/463 |
| 3,860,631 | 1/1975 | Gleason et al. | 560/29 |
| 3,882,161 | 5/1975 | Eichenberger et al. | |

OTHER PUBLICATIONS

Umezawa et al., J. Antibiotics, vol. 29, pp. 97–99 (1976).
Suda et al., J. Antibiotics, vol. 29, pp. 100–101 (1976).
Nakamura, J. Antibiotics, vol. 29, pp. 102–103 (1976).
Suda et al., J. Antibiotics, vol. 29, pp. 600–601 (1976).
Umezawa et al., J. Antibiotics, vol. 29, pp. 857–859 (1976).

*Primary Examiner*—James H. Reamer
*Attorney, Agent, or Firm*—Herbert W. Taylor, Jr.

[57] ABSTRACT

Bestatin, which is [(2S,3R)-3-amino-2-hydroxy-4-phenylbutanoyl]-L-leucine, and related compounds which inhibit aminopeptidase B, leucino aminopeptidase and Bleomycin hydrolase, enhance the anti-tumor effect of Bleomycin and exhibit an antifertility effect were synthesized and tested.

27 Claims, No Drawings

BESTATIN

CROSS-REFERENCE TO RELATED APPLICATIONS

This application is a continuation of copending application Ser. No. 868,571, filed Jan. 10, 1978, now abandoned, which is a division of our prior, copending application Ser. No. 809,835 filed June 24, 1977, now U.S. Pat. No. 4,189,604, which is a continuation-in-part of application Ser. No. 800,820 filed May 26, 1977 which is a continuation-in-part of copending application Ser. No. 703,863 filed July 9, 1976 and now abandoned. Ser. No. 800,820 has also been abandoned.

BACKGROUND OF THE INVENTION

1. Field of the Invention

This invention relates to chemical compounds of the peptide type produced by synthetic methods and includes various processes.

2. Description of the Prior Art

Bestatin is a chemical active as an inhibitor of certain enzymes which was originally produced by fermentation of *Streptomyces olivoreticuli* as disclosed in various patents (see Farmdoc 09548X) and the following publications:

1. Umezawa, H.; T. Aoyagi, H. Suda, M. Hamada & T. Takeuchi: Bestatin an Inhibitor of Aminopeptidase B, Produced by Actinomycetes. J. Antibiotics 29:97–99, 1976.
2. Suda, H.; T. Takita, T. Aoyagi & H. Umezawa: The Structure of Bestatin. J. Antibiotics 29:100–101, 1976.
3. Nakamura, H.; H. Suda, T. Takita, T. Aoyagi, H. Umezawa & Y. Iitaka: X-Ray Structure Determination of (2S,3R)-3-amino-2-hydroxy-4-phenyl-butanoic Acid, a New Amino Acid Component of Bestatin. J. Antibiotics 29:102–103, 1976.
4. Suda, H.; T. Takita, T. Aoyagi and H. Umezawa: The Chemical Synthesis of Bestatin. J. Antibiotics 29:600–601, 1976.
5. Umezawa, H.; M. Ishizuka, T. Aoyagi and T. Takeuchi, Enhancement of Delayed-Type Hypersensitivity by Bestatin, an Inhibitor of Aminopeptidase B and Leucine Aminopeptidase, J. Antibiotics 29, 857–859, 1976.

Bestatin has the chemical name [(2S,3R)-3-amino-2-hydroxy-4-phenylbutanoyl]-L-leucine and the following structure

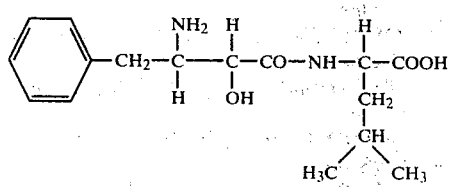

SUMMARY OF THE INVENTION

According to the present invention, there is provided a compound represented by the following formula (I):

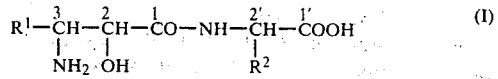

where $R^1$ is a group selected from a group consisting of lower alkyl group, cycloalkanoalkyl group, phenyl group, benzyl group and substituted benzyl group; $R^2$ is a group selected from a group of alkyl group having 1 to 6 carbon atoms, hydroxyalkyl group, mercaptoalkyl group, carboxamidoalkyl group, alkoxyalkyl group, alkylmercaptoalkyl group, carboxyalkyl group, aryl group, aralkyl group and substituted aralkyl group. In the case when $R^1$ is benzyl group and $R^2$ is isobutyl group, the configuration of the compound is only (2S,3R,2'R), (2S,3S,2'S) or (2S,3S,2'R).

Bestatin is (2S,3R)-3-amino-2-hydroxy-4-phenylbutanoyl-(S)-leucine which is a compound represented by said Formula (I) wherein $R^1$ is a benzyl group and $R^2$ an isobutyl group.

A preferred embodiment of the present invention is a compound having the formula

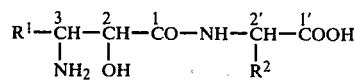

wherein $R^1$ is (lower)alkyl, cyclopentylmethyl, cyclohexylmethyl, cycloheptylmethyl or

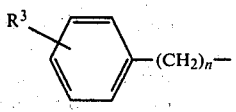

wherein
$R^3$ is hydrogen, chloro, methyl, nitro, hydroxy or amino and n is 0 or 1 and
$R^2$ is (lower)alkyl having 1 to 6 carbon atoms, hydroxy(lower)alkyl, alkylthioalkyl, carboxamido(-lower)alkyl, carboxy(lower)alkyl, phenyl or benzyl provided that when $R^1$ is benzyl and $R^2$ is isobutyl the configuration of the compound is (2S,3R,2'R), (2S,3S,2'S) or (2S,3S,2'R).

Another preferred embodiment of the present invention is a compound having the formula

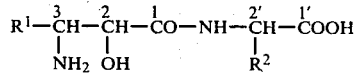

wherein $R^1$ is (lower)alkyl, cyclopentylmethyl, cyclohexylmethyl, cycloheptylmethyl or

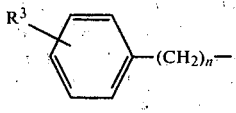

wherein
$R^3$ is hydrogen, chloro, methyl, nitro, hydroxy or amino and n ix 0 or 1 and
$R^2$ is (lower)akyl having 1 to 6 carbon atoms, hydroxymethyl, methylthioethyl, —CH$_2$CH$_2$CONH$_2$, —CH$_2$CH$_2$COOH, phenyl or benzyl provided that when $R^1$ is benzyl and $R^2$ is isobutyl the configuration of the compound is (2S,3R,2'R), (2S,3S,2'S) or (2S,3S,2'R).

Another preferred embodiment of the present invention is a compound having the formula

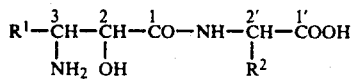

wherein
R¹ is (lower)alkyl, cyclopentylmethyl, cyclohexylmethyl or cycloheptylmethyl, and
R² is (lower)alkyl having 1 to 6 carbon atoms, hydroxymethyl, methylthioethyl, —CH₂CH₂CONH₂, —CH₂CH₂COOH, phenyl or benzyl.

Another preferred embodiment of the present invention is a compound having the formula

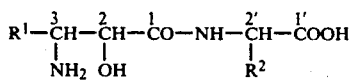

wherein R¹ is

wherein
R³ is hydrogen, chloro, methyl, nitro, hydroxy or amino and
R² is (lower)alkyl having 1 to 6 carbon atoms, hydroxymethyl, methylthioethyl, —CH₂CH₂CONH₂, —CH₂CH₂COOH, phenyl or benzyl.

Another preferred embodiment of the present invention is a compound having the formula

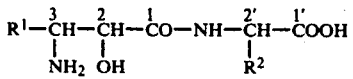

wherein R¹ is

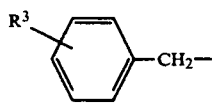

wherein
R³ is hydrogen, chloro, methyl, nitro, hydroxy or amino and
R² is (lower)alkyl having 1 to 6 carbon atoms, hydroxymethyl, methylthioethyl, —CH₂CH₂CONH₂, —CH₂CH₂COOH, phenyl or benzyl provided that when R¹ is benzyl and R² is isobutyl the configuration of the compound is (2S,3R,2'R), (2S,3S,2'S) or (2S,3S,2'R).

Another preferred embodiment of the present invention is a compound having the formula

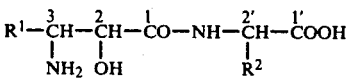

wherein R¹ is

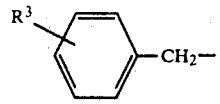

wherein
R³ is chloro, methyl, nitro, hydroxy or amino and
R² is (lower)alkyl having 1 to 6 carbon atoms, hydroxymethyl, methylthioethyl, —CH₂CH₂CONH₂, —CH₂CH₂COOH, phenyl or benzyl.

Another preferred embodiment of the present invention is a compound having the formula

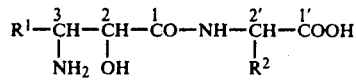

wherein R¹ is

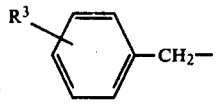

wherein
R³ is chloro, methyl, nitro, hydroxy or amino and
R² is (lower)alkyl having 1 to 6 carbon atoms.

Another preferred embodiment of the present invention is a compound having the formula

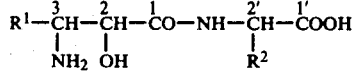

wherein R¹ is

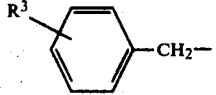

wherein
R³ is hydrogen, chloro, methyl, nitro, hydroxy or amino and
R² is (lower)alkyl having 1 to 6 carbon atoms provided that when R¹ is benzyl and R² is isobutyl the configuration of the compound is (2S,3R,2'R), (2S,3S,2'S) or (2S,3S,2'R).

Preferred species of the present invention include the following:
(2S,3R)-3-amino-2-hydroxy-4-phenylbutanoyl-(R)-leucine,
(2S,3S)-3-amino-2-hydroxy-4-phenylbutanoyl-(R)-leucine,
(2S,3S)-3-amino-2-hydroxy-4-phenylbutanoyl-(S)-leucine,
(2S,3R)-3-amino-2-hydroxy-4-p-nitrophenylbutanoyl-(S)-leucine,
(2S,3R)-3-amino-2-hydroxy-4-phenylbutanoyl-(S)-valine,
(2S,3S)-3-amino-2-hydroxy-4-phenylbutanoyl-(S)-norvaline,
(2S,3R)-3-amino-2-hydroxy-4-phenylbutanoyl-(S)-methionine, (2S,3R)-3-amino-2-hydroxy-4-phenylbutanoyl-(S)-isoleucine, (2S,3R)-3-amino-2-hydroxy-4-phenylbutanoyl-(S)-norleucine, (2RS,3RS)-3-amino-2-hydroxy-4-p-chlorophenylbutanoyl-(S)-leucine, (2RS,3RS)-3-amino-2-hydroxy-4-o-chlorophenylbutanoyl-(S)-leucine, (2RS,3RS)-3-amino-2-hydroxy-4-p-methylphenylbutanoyl-(S)-leucine, and (2RS,3R)-3-amino-2-hydroxy-4-p-aminophenylbutanoyl-(S)-leucine.

(2RS,3RS)-3-amino-2-hydroxy-4-p-hydroxyphenylbutanoyl-(S)-leucine.

(2S,3R)-3-amino-2-hydroxy-4-p-hydroxyphenylbutanoyl-(S)-leucine.

The invention also includes a process for the preparation of the compounds represented by Formula (I) in the following manner:

A nitrile derivative as represented by a formula (II),

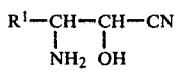

(wherein $R^1$ is a group as defined above) or such a nitrile derivative whose amino group is protected is hydrolyzed with an acid to prepare an amino acid as represented by a formula (III),

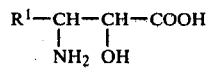

(wherein $R^1$ is a group as defined above). After having protected, if necessary, the functional groups which do not take part in the reaction, this amino acid and an amino acid represented by the formula (IV)

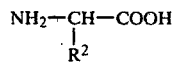

(wherein $R^2$ is a group as defined above) are condensed in the ordinary peptide linking method. When said protected groups are removed, the compounds as represented by Formula (I) are obtained.

There is also provided by the present invention a process for producing a peptide represented by the formula

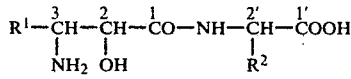

(wherein $R^1$ and $R^2$ are groups as defined above) comprising consecutive steps in which a nitrile represented by the formula

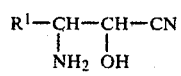

(wherein $R^1$ is a group as defined above) or a nitrile derivative whose amino group is protected is hydrolyzed with an acid to prepare an amino acid represented by the formula

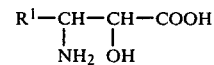

(wherein $R^1$ is a group as defined above); after having protected, if necessary, the functional groups which do not participate in the reaction, the resulting amino acid and an amino acid as represented by the formula

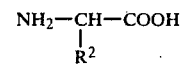

(wherein $R^2$ is a group as defined above) are condensed in an ordinary peptide linking process; and then said protecting group is removed and, preferably, said process wherein $R^1$ is benzyl or substituted benzyl and $R^2$ is alkyl or hydroxymethyl having 3 or 4 carbon atoms and also said process wherein $R^1$ is benzyl and $R^2$ is alkyl having 4 carbon atoms and also said process wherein the acid which is employed for hydrolysis is hydrochloric acid, hydrobromic acid or sulfuric acid.

There is also provided by the present invention a process for collecting an antipode comprising consecutive steps i which an amino acid represented by the formula

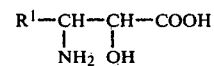

(wherein $R^1$ is a group as defined above) is protected by benzyloxycarbonyl; the thusly protected amino acid is allowed to react with brucine to prepare a diastereoisomer of brucine salt; and said diastereoisomer is optically resolved in an organic solvent and preferably said process wherein $R^1$ is benzyl, and also said process wherein ethyl acetate is used as the organic solvent.

There is further provided by the present invention a process for collecting an antipode comprising consecutive steps in which an amino acid represented by the formula

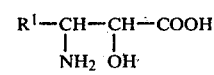

(wherein $R^1$ is a group as defined above) is protected by benzyloxycarbonyl; the thusly protected amino acid is dissolved in an organic solvent selected from a group of alcohols, ethers, esters, ketones, halogenated hydrocarbons, dimethylformamide, dimethylacetamide and acetonitrile; then to the resulting solution an organic solvent selected from a group of petroleum hydrocarbons, aromatic hydrocarbons, hexane and cyclohexane is added so as to optically resolve the same and preferably said process wherein $R^1$ is benzyl and also said process wherein the organic solvents are ethyl acetate and petroleum ether.

There is also provided by the present invention a compound represented by the formula

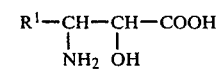

wherein R¹ is lower alkyl, phenyl, benzyl and substituted benzyl and particularly is
(2S,3R)-3-amino-2-hydroxy-4-phenylbutanoic acid,
(2S,3R)-3-amino-2-hydroxy-4-p-hydroxyphenylbutanoic acid,
(2RS,3RS)-3-amino-2-hydroxy-4-phenylbutanoic acid,
(2RS,3RS)-3-amino-2-hydroxy-4-p-hydroxyphenylbutanoic acid,
(2RS,3RS)-3-amino-2-hydroxy-4-p-chlorophenylbutanoic acid,
(2RS,3RS)-3-amino-2-hydroxy-4-o-chlorophenylbutanoic acid,
(2RS,3RS)-3-amino-2-hydroxy-4-p-methylphenylbutanoic acid or
(2RS,3RS)-3-amino-2-hydroxy-4-p-benzyloxyphenylbutanoic acid.

Typical examples of nitrile derivatives as represented by Formula (II) are 3-amino-2-hydroxypropionitrile, 3-amino-2-hydroxy-5-methylhexanonitrile, 3-amino-2-hydroxy-3-phenylpropionitrile, 3-amino-2-hydroxy-4-p-chlorophenylbutyronitrile, 3-amino-2-hydroxy-4-phenylbutyronitrile, 3-amino-2-hydroxy-4-o-chlorophenylbutyronitrile, 3-amino-2-hydroxy-4-p-methylphenylbutyronitrile, 3-amino-2-hydroxy-4-p-hydroxyphenylbutyronitrile and 3-amino-2-hydroxy-4-p-benzyloxyphenyl-butyronitrile. Any known amino-protected group such as those employed in peptide chemistry may be used for protection of the amino groups. Preferred examples of acyl type amino-protecting groups are a formyl group, an acetyl group, a trifluoroacetyl group, substituted or non-substituted benzoyl group; examples of urethane type amino-protecting groups are substituted or non-substituted benzyloxycarbonyls, alkoxycarbonyl group having 1 to 6 carbon atoms and cycloalkanoyxcarbonyl group; preferred examples of other amino-protecting groups are substituted or non-substituted arylsulfonyl group, phthalyl group, o-nitrophenylsulphenyl group or trityl group. Any type of acid usually employed for hydrolyzing nitriles may be used in the present invention for hydrolysis. Examples of inorganic acids include hydrochloric acid, hydrobromic acid and sulfuric acid; examples of organic acids include alkylsulfonic acids such as methanesulfonic acid, ethanesulfonic acid, arylsulfonic acid such as benzenesulfonic acid and toluenesulfonic acid. The concentration of these acids may be at any level usable for hydrolyzing ordinary nitriles. However, a concentration of above 1 N will be preferred.

To the compounds whose amino group is protected and which are not readily dissolved in the aqueous solution of acid, an organic solvent which is miscible with water such as tetrahydrofuran, dioxane, lower alcohols, acetone, dimethylformamide, dimethylacetamide and dimethylsulfoxide may be added to enhance the solubility of the compounds in the aqueous solution.

In the case when a protecting group is employed, if the protecting group is removed furing the hydrolysis to form electrophilic bodies, a cation scavenger such as anisole may be added. The hydrolytic temperature may be at any level within the range from room temperature to the temperature at which reflux of the reaction mixture takes place. To isolate the desired amino acid from the reaction mixture, any ordinary method for isolating amino acid may be applied. For example, when the hydrolysis is effected with a volatile acid, the excessive acid may be removed by concentrating the reaction mixture under reduced pressure and the residue dissolved in water and neutralized with aqueous alkali solution to the isoelectric point. Then, if necessary, acetone, methanol or ethanol is added to the reaction mixture to crystallize the intended compound as represented by Formula (III), which is then separated by filtration. Or otherwise, when a non-volatile acid is used the reaction mixture is diluted with water to less than 1 N acid and allowed to pass through a strong acidic ion exchange resin so that the desired amino acid can be adsorbed to the ion exchange resin. The adsorbed amino acid is eluted from the ion exchange resin with a volatile alkali such as ammonia water and condensed under reduced pressure. If necessary acetone, methanol or ethanol is added to crystallize the intended compound as represented by Formula (III), which is then separated by filtration.

In the foregoing reaction, when an (R)-nitrile derivative is used as a starting material, (2RS,3R)-amino acid is obtained; when an (S)-nitrile derivative is used, (2RS,3S)-amino acid is obtained: when an (RS)-nitrile derivative is used, (2RS,3RS)-amino acid is obtained.

The compounds obtained as represented by Formula (III) can be used as a raw material in the process as described hereinbelow. For example, 3-amino-2-hydroxy-4-phenylbutanoic acid (hereinafter, this amino acid is abbreviated as AHPA) which is a precursor of Bestatin is in (2S,3R) form. Therefore, in order to obtain this compound, it is necessary to resolve (2RS,3R)-AHPA to (2S,3R)- and (2R,3R)-AHPA.

(2RS,3R)-AHPA can be resolved optically in ethyl acetate in the form of diastereoisomer which is obtained by first benzyloxycarbonylation of (2RS,3R)-AHPA in the ordinary manner to prepare benzyloxycarbonyl-(2R,3R)-AHPA, which is then allowed to react with brucine (hereinafter, benzyloxycarbonyl group is abbreviated as Z). More specifically, Z-(2RS,3R)-AHPA and an equivalent or slightly excessive quantity of brucine are dissolved in ethyl acetate under heating and then filtered, if necessary. When the filtrate is cooled or allowed to cool, a crystal will be deposited. This crystal is separated by filtration and, if necessary, recrystallizing operations from ethyl acetate are repeated to prepare the optically pure brucine salt of Z-(2S,3R)-AHPA. When this brucine salt is treated in the ordinary way, optically pure Z-(2S,3R)-AHPA is obtained. Otherwise optically pure Z-(2R,3R)-AHPA may be prepared as follows: A solution of ethyl acetate containing a brucine salt of Z-(2R,3R)-AHPA and a small quantity of Z-(2S,3R)-AHPA is shaken with dilute hydrochloric acid to remove brucine, the ethyl acetate layer is dried with a dehydrating agent such as anhydrous sodium sulfate and concentrated under reduced pressure. Then the residue is dissolved into a small quantity of ethyl acetate. Upon adding petroleum ether there is obtained crystals which may then be separated by filtration to prepare optically pure Z-(2R,3R)-AHPA.

It was noted that the (2R,3R)-form of Z-AHPA had smaller solubilities into an organic solvent than the (2S,3R)-form. Z-(2RS,3R)-AHPA is dissolved in a first soluble solvent at room temperature or under heating. Then a second insoluble solvent is added so as to precipitate crystals, which are then separated by filtration. If necessary, the foregoing operation is repeated until optically pure Z-(2R,3R)-AHPA is obtained.

The first soluble solvent may include lower alcohols such as methanol, ethanol and propanol; ethers such as diethyl ether, diisopropyl ether, tetrahydrofuran and dioxane; esters such as methyl acetate and ethyl acetate; ketones such as acetone and methyl ethyl ketone; halogenated hydrocarbons such as methylene chloride and chloroform; amides such as dimethylformamide and dimethylacetamide; and nitriles such as acetonitrile, etc. The second insoluble solvent may include petroleum hydrocarbons such as petroleum ether, petroleum benzene and ligroin; aromatic hydrocarbons such as benzene and toluene; alkanes such as pentane and hexane; and cyclohexanes such as cyclopentane and cyclohexane. By use of the diastereoisomer method employing brucine, the optically impure Z-(2S,3R)-AHPA present in the filtrate may be purified to optically pure (2S,3R)-AHPA.

Z-AHPA as used in the above-mentioned resolution may be synthesized by Schotten-Baumann method in the presence of an alkali by reaction of (2RS,3R)-AHPA and benzyloxycarbonyl chloride or, otherwise, in the presence of an organic tertiary base such as triethylamine and N-methylmorpholine by reaction with a benzyloxycarbonylating reagent such as benzyloxycarbonyl-p-nitrophenyl ester, benzyloxycarbonyl azide, benzyloxycarbonyl-N-hydroxysuccinimide ester and benzyloxycarbonyl-4,6-dimethyl-2-mercaptopyrimidine in a solvent prepared by mixing dioxane, tetrahydrofuran, acetonitrile or dimethylformamide with water.

Although the foregoing optical resolution has been described with respect to AHPA, a similar optical resolution may be effected, if necessary, for the other amino acids.

To prepare Bestatin and its related compounds as represented by Formula (I), an amino acid as represented by Formula (III) is condensed with a compound as represented by Formula (IV) in the ordinary peptide linking method and then the protecting groups, which, if necessary have been used for protecting the functional groups which do not take part in the reaction, are removed.

Typical examples of amino acids are glycine, alanine, 2-amino-butanoic acid, valine, norvaline, leucine, norleucine, isoleucine, tertiary-leucine, 2-aminoheptanoic acid, 2-amino-5-methylhexanoic acid, 2-aminooctanoic acid, 2-amino-6-methylheptanoic acid, serine, threonine, allothreonine, cysteine, homocysteine, asparagine, glutamine, O-methylserine, O-ethylserine, O-propylserine, methionine, ethionine, aspartic acid, glutamic acid, phenylglycine, p-methoxyphenylglycine, phenylalaline, tyrosine, p-methoxyphenylalanine and p-nitrophenylalanine.

The method for condensing an amino acid as represented by Formula (III) and an amino acid as represented by Formula (IV) includes a carbodiimide method wherein dicyclohexylcarbodiimide or 1-ethyl-3-(3-dimethylaminopropyl)carbodiimide is used; an azide method employing nitrous acid or alkyl nitrite; a mixed anhydride method employing ethyl chloroformate or isobutyl chloroformate; an active ester method employing cyanomethyl ester, vinyl ester, substituted and non-substituted phenyl esters, thiophenyl ester of N-hydroxysuccinimide ester; an O-acyl hydroxylamine derivative method employing O-acylacetoxime or O-acylcyclohexanonneoxime; an N-acyl derivative method employing carbonyldiimidazole.

Organic solvents using in the above condensation reaction may be ethers such as diethyl ether, tetrahydrofuran or dioxane; esters such as ethyl acetate or methyl acetate; ketones such as acetone or methyl ethyl ketone; halogenated hydrocarbons such as methylene chloride or chloroform; amides such as dimethylformamide or dimethylacetamide; nitriles such as acetonitrile.

In the case when an amino acid is represented by Formula (III) and whose amino group is protected and an amino acid as represented by Formula (IV) whose carboxyl group is not protected are condensed in an active ester method, a mixed solvent of water and water miscible organic solvent may be used in the presence of an inorganic base such as sodium bicarbonate, magnesium oxide or an organic tertiary base such as triethylamine or N-methylmorpholine.

Protecting groups in the resulting compound may be removed by the usual method in peptide chemistry such as catalytic hydrogenation on palladium, saponification with an alkali, acidolysis with hydrogen bromide in acetic acid, with trifluoroacetic acid, with hydrogen chloride in dioxane, tetrahydrofuran or ethyl acetate, with liquid hydrogen fluoride, hydrazinolysis with hydrazine or treatment with sodium in liquid ammonia. Thus, the intended substance as represented by Formula (I) is obtained.

The nitrile derivatives as represented by Formula (II) and used in this invention as the starting material may be synthesized reducing an α-amino acid, whose amino group is being protected and carboxyl group converted to an amide by reaction with a secondary amine, at low temperature less than 0° C. with a metal hydride in ethers such as diethyl ether or tetrahydrofuran to prepare an amino-aldehyde whose amino group is protected. The resulting amino-aldehyde is then converted to the adduct with sodium bisulfite and then allowed to react with an alkaline metal cyanide or directly allowed to react with hydrogen cyanide to prepare cyanohydrin, or 3-amino-2-hydroxynitrile.

Preferred examples of the secondary amine are N,N-dimethylamine, aziridine, N-methylaniline, carbazole, 3,5-dimethylpyrazole and imidazole. Preferred examples of metal hydride are lithium aluminum hydride, lithium di- and tri-alkoxyaluminum hydride and sodium bis(2-methoxyethoxy)aluminum hydride. Examples of the protecting group for the amino group are the protecting groups usually employed in the peptide chemistry. Urethane type protecting groups may be used preferably and, above all, benzyloxycarbonyl group may be preferred.

According to a second method a lower alkyl ester of α-amino acid whose amino group is protected by an amino-protecting group similar to those mentioned previously is reduced at a temperature lower than −40° C. in aromatic hydrocarbons such as toluene or benzene and ethers such as diethyl ether or tetrahydrofuran with metal hydrides such as sodium aluminum hydride, diisobutylaluminum hydride or sodium bis(2-methoxyethoxy)aluminum hydride thereby to prepare aminoaldehyde whose amino group is protected. When such an aminoaldehyde has been treated in the above-mentioned manner, 3-amino-2-hydroxynitriles are prepared.

The physiological activities of Bestatin and its related compounds represented by Formula (I) prepared in the present invention were determined as follows:

(A) Inhibitory activity against aminopeptidase B

Testing method

The method described by V. K. Hopusu, K. K. Makinen, G. G. Glenner in Archives of Biochemistry and Biophysics 114, 557, (1966) was modified. To the mixture of 0.3 ml. of 1 mM arginine β-naphthylamide and 1.0 Ml. of 0.1 M Tris hydrochloride buffer (pH 7.0), 0.7 Ml. of distilled water with or without a test material is added and warmed at 37° C. for 3 minutes. The reaction is started by addition of 0.2 ml. of aminopeptidase B solution which is prepared by Sephadex 100 chromatography as described by Hopusu et al. After 30 minutes at 37° C., 0.6 ml. of 1.0 M acetate buffer (pH 4.2) containing diazonium salt of o-aminoazotoluene at 1.0 mg./ml. and Tween 20 at 1.0% is added. Fifteen minutes at room temperature thereafter, absorbance (a) at 530 nm is measured by spectrophotometer. As the control, by similar means the absorbance (b) after the reaction in the absence of a sample is measured. The inhibition percent is calculated as follows: $(b-a)/b \times 100$.

Inhibition percentages at various concentrations were measured and from the measured inhibition percentages, 50% inhibitions ($ID_{50}$) were deduced. The results are as listed in Table 1.

Table 1.

Inihibitory Activity of Bestatin and Its Related Compounds Against Aminopeptidase B

| No. | Compound | $ID_{50}$(mcg./ml.) |
|---|---|---|
| 1 | (2S,3R)-AHPA-(S)—Leu | 0.10 |
| 2 | (2S,3S)-AHPA-(S)—Leu | 1.25 |
| 3 | (2S,3R)-AHPA-(R)—Leu | 0.56 |
| 4 | (2S,3S)-AHPA-(R)—Leu | 0.04 |
| 5 | (2S,3R)-AHPA—Gly | 21.5 |
| 6 | (2S,3R)-AHPA-(S)—Val | 0.55 |
| 7 | (2S,3R)-AHPA-(S)—ILe | 0.05 |
| 8 | (2S,3R)-AHPA-(S)—Met | 0.22 |
| 9 | (2S,3R)-AHPA-(S)—Gln | 1.2 |
| 10 | (2S,3R)-AHPA-(S)—Nva | 0.17 |
| 11 | (2S,3R)-AHPA-(S)—Nle | 0.13 |
| 12 | (2S,3R)-AHPA-(S)—Phe | 4.2 |
| 13 | (2S,3R)-AHPA-(S)—Ser | 0.72 |
| 14 | (2S,3R)-AHPA-(S)—Glu | 25 |
| 15 | (2S,3R)-AHPA-(RS)—Acc | 3.1 |
| 16 | (2RS,3R)-Me—Ise-(S)—Leu | 16 |
| 17 | (2RS,3R)-iso—Bu—Ise-(S)—Leu | 12 |
| 18 | (2RS,3R)-Ph—Ise-(S)—Leu | 56 |
| 19 | (2RS,3RS)-AHPA(p-Cl)-(S)—Leu | 0.07 |
| 20 | (2RS,3RS)-AHPA(o-Cl)-(S)—Leu | 0.48 |
| 21 | (2RS,3RS)-APHA(p-Me)-(S)—Leu | 0.01 |
| 22 | (2S,3R)-AHPA(p-$NO_2$)-(S)—Leu | 0.01 |
| 23 | (2S,3R)-APHA(p-$NH_2$)-(S)—Leu | 0.10 |
| 24 | (2S,3R)-AHPA(6H)-(S)—Leu | 1.05 |

Note:
In the Table, Leu, leucine; Gly, glycine; Ser, serine; Gln, glutamine; Glu, glutamic acid; Val, valine; Nva, norvaline; Met, methionine; Ile, isoleucine; Nle, norleucine; Acc, 2-aminooctanic acid; Phe, phenylalanine; Me-Ise, β-methylisoserine (3-amino-2-hydroxy-propionic acid); iso—Bu—Ise, β-isobutylisoserine (3-amino-2-hydroxy-5-methylhexanoic acid); Ph—Ise, β-phenylisoserine (3-amino-2-hydroxy-3-phenylpropionic acid); AHPA(p-Cl), 3-amino-2-hydroxy-4-p-chlorophenylbutanoic acid; AHPA(o-Cl), 3-amino-2-hydroxy-4-o-chlorophenylbutanoic acid; AHPA(p-Me), 3-amino-2-hydroxy-4-p-methylphenylbutanoic acid; AHPA(p-$NO_2$), 3-amino-2-hydroxy-4-p-nitrophenylbutanoic acid; AHPA(p-$NH_2$), 3-amino-2-hydroxy-4-p-aminophenylbutanoic acid; AHPA(6H), 3-amino-2-hydroxy-4-cyclohexylbutanoic acid.

(B) Organ distribution of Bleomycin in the presence of Bestatin 100 mg./kg. of Bleomycin $B_2$ was subcutaneously administered to each of three ICR male mice (4 weeks of age) and 100 mg./kg. of Bleomycin $B_2$ and 100 mg./kg. of Bestatin were subcutaneously administered simultaneously to each of three similar mice. These 6 mice were killed one hour after administration and the quantity of Bleomycin $B_2$ remaining in the serum and organs was determined by a thin layer disc method employing *Bacillus subtilis* PCI219 as the test microorganism. The results are as listed in Table 2, wherein the numerals show average values in mcg./ml.

Table 2.

The Effect of Simultaneous Administration of Bestatin and Bleomycin $B_2$ on Organ Distribution of Bleomycin in Mice.

| | | Serum | Lung | Skin | Liver | Kidney | Spleen | Stomach | Brain |
|---|---|---|---|---|---|---|---|---|---|
| BLM 100 mg/kg | | 110 | 11.2 | 4.5 | 0 | 68.0 | 4.0 | 1.6 | 0 |
| BLM 100 mg/kg BST 100 mg/kg | + | 140 | 21.2 | 42.0 | 0 | 84.0 | 5.8 | 2.5 | 2.4 |

Note:
BLM, Bleomycin $B_2$; BST, Bestatin (C) Contraceptive property

Antifertility of Bestatin

Immediately after subcutaneously administering Bestatin (10 mg./kg.) to ICR JCL female mice at the age of puberty, these mice were placed with male mice of similar line. Female mice which had copulated were killed two days after formulation of vaginal plug and the ova were collected from their uterine tubes so as to examine whether they had been fertilized or not. The fertilized ova were at 8–16 cell period.

| Bestatin-administered Mouse Group | Female No. 1 | Female No. 2 | Total N = 2 |
|---|---|---|---|
| Number of corpus luteum | 10 | 19 | 29 |
| Number of collected ovum | 10 | 19 | 29 |
| Fertilized ovum | 4 (40%) | 6 (31.6%) | 10 (34.5%) |
| Non-fertilized ovum | 6 (60%) | 13 (68.4%) | 19 (65.5%) |

| Control | Female No. 1 | Female No. 2 | Total N = 2 |
|---|---|---|---|
| Number of corpus luteum | 13 | 13 | 26 |
| Number of collected ovum | 9 | 11 | 20 |
| Fertilized ovum | 6 (66.7%) | 8 (72.7%) | 14 (70%) |
| Non-fertilized ovum | 3 (33.3%) | 3 (27.3%) | 6 (30%) |

The experiments showed that the fertility of the ova collected from the mice, which had copulated 4–16 hours after administration of Bestatin, was 34.5%, whereas the fertility of the ova collected from the control mouse group was 70%. It is apparent from these results that Bestatin has an antifertility property.

Following is a discussion by way of example only of methods of carrying the invention into effect. However, it should be noted herein that any suitable functional group-protecting methods, functional group-removing methods and peptide linkage-forming methods other than those described hereinbelow may be employed. In addition to the aforementioned abbreviations, the following abbreviations are also used in the examples:
HOBt, N-hydroxybenzotriazole; DCCD, N,N'-dicyclohexylcarbodiimide, HOSu, N-hydroxysuccinimide; —OBzl.TosOH, benzyl ester p-toluenesulfonate; —OSu, N-hydroxysuccinimide ester; —OMe, methyl ester; —ONb, p-nitrobenzyl ester; Boc, t-butoxycarbonyl; DCHA, dicyclohexylamine; —OBu$^t$ tert.-butyl ester.

Rf value is measured on a silica gel $GF_{254}$ plate prepared by Merck Corp. using a BuOH: AcOH: $H_2O$ (4:1:1) as developing solvent.

A few 3-amino-2-hydroxycarboxylic acids and their containing peptides possess two Rf values because they are a mixture of threo- and erythro- configurations.

DESCRIPTION OF THE PREFERRED EMBODIMENTS

EXAMPLE 1

Step 1

35.4 g of oily Z-(2RS,3R)-3-amino-2-hydroxy-4-phenylbutyronitrile is dissolved in a mixture of 300 ml. of concentrated hydrochloric acid and 300 ml. of dioxane. After adding 21.2 g. of anisole, the reaction mixture is refluxed for 12 hours. Then dioxane is distilled away under reduced pressure, the resulting solution of hydrochloric acid is washed with ether and the water layer is concentrated under reduced pressure and evaporated to dryness. Subsequently, 200 ml. of water is added to the residual substance and the insoluble substance is separated by filtration. After adding an equal quantity of acetone, the mixture is adjusted to pH 5.5 with ammonia water. The mixture is allowed to stand in a refrigerator. The deposited crystals are seprated by filtration, 13.66 g. of intended (2RS,3R)-AHPA is obtained.

$[\alpha]_{578}^{27} +16.8°$ (c 1.25, N HCl), Rf 0.23 and 0.26, Anal. for $C_{10}H_{13}NO_3$, Found C: 61.06, H: 6.55, N: 6.80; Calc'd. C: 61.52, H: 6.71; N: 7.18.

Step 2

13.66 g. of (2RS,3R)-AHPA obtained in Step 1 is dissolved in 70 ml. of 1 N sodium hydroxide solution. While vigorously agitating the solution under cooling with ice, 15 ml. of Z-Cl and 70 ml. of 1 N sodium hydroxide solution are added in three portions over a period of 30 minutes. Then the reaction mixture is vigorously agitated for 1 hour under cooling with ice and for 3 hours at room temperature.

When the reaction has been completed, 6 N hydrochloric acid is added to adjust the reaction mixture to pH 1. As a result, oily material is separated which is then extracted twice with 100 ml. of ethyl acetate. The ethyl acetate layer is washed with water and dehydrated to dryness by use of anhydrous magnesium sulfate. After separating magnesium sulfate by filtration, the filtrate is concentrated under reduced pressure and the residue is crystallized in ethyl acetate-petroleum ether to prepare 8.48 g. of optically impure Z-(2R,3R)-AHPA. On the other hand, when the mother liquor is concentrated under reduced pressure and the residue is crystallized in petroleum ether, 8.07 g. of optically impure Z-(2S,3R)-AHPA is obtained.

m.p. 142°–143° C., $[\alpha]_{578}^{23} +70.2°$ (c 1.44, AcOH).

8.00 g. of optically impure Z-(2S,3R)-AHPA and 10.35 g. of brucine dihydrate are dissolved under heating in a mixture of 300 ml. of ethyl acetate and 10 ml. of methanol and filtered. When the filtrate is allowed to cool, the brucine salt of Z-(2S,3R)-AHPA is separated. Then the crystal separated by filtration is recrystallized twice from ethyl acetate to prepare 13.51 g. of pure brucine salt of Z-(2S,3R)-AHPA.

m.p. 144° C. $[\alpha]_{578}^{21} +33.8°$ (c 1.12, AcOH).

13.5 g. of the obtained crystal is suspended in 150 ml. of ethyl acetate and brucine is removed with 30 ml. of 1 N hydrochloric acid. Then the ethyl acetate layer is washed with water and dehydrated to dryness by use of anhydrous magnesium sulfate. Subsequently, magnesium sulfate is separated by filtration and ethyl acetate is distilled away under reduced pressure. When the residue is reprecipitated from ethyl acetate-petroleum ether, 6.21 g of Z-(2S,3R)-AHPA is obtained.

m.p. 154.5° C., $[\alpha]_{578}^{24} +83.5°$ (c 1.34, AcOH).

Step 3

2.25 g. of Z-(2S,3R)-AHPA and 945 mg. of HOBt are dissolved in 70 ml. of tetrahydrofuran. After adding 2.75 g. of Leu-OBzl.TosOH, the mixture is neutralized with 0.98 ml. of triethylamine and cooled to −5° C. Then 1.40 g. of DCCD is added and the reaction mixture is allowed to stand overnight for reaction. Tetrahydrofuran is distilled away under reduced pressure and 200 ml. of ethyl acetate is added. After filtering off the insoluble substances, the filtrate is washed with 1 N sulfuric acid, water, 5% aqueous sodium bicarbonate solution and water in that order and then dehydrated to dryness with anhydrous magnesium sulfate. The residue obtained by concentrating the filtrate under reduced pressure is solidified in ethyl acetate-petroleum ether. Recrystallization from the same solvent gives 3.26 g. of Z-(2S,3R)-AHPA-(S)-Leu-OBzl.

m.p. 122°–123° C., $[\alpha]_{578}^{23} +14.2°$ (c 1, AcOH), Anal. for $C_{31}H_{36}N_2O_6$, Found C: 69.66; H: 7.01; N: 5.13; Calc'd. C: 69.90, H: 6.81; N: 5.26.

Step 4

3.22 g. of 2-(2S,3R)-AHPA-(S)-Leu-OBzl is dissolved in 100 ml. of methanol and hydrogenated for 3 hours with 100 mg. of palladium black. The catalyst is filtered off and the solvent is concentrated under reduced pressure. When a recrystallization operation is carried out with methanol-ethyl acetate, 889 mg. of (2S,3R)-3-amino-2-hydroxy-4-phenylbutanoyl-(S)-leucine is obtained.

m.p. 208°–213° C. (decomp.), $[\alpha]_{578}^{21} -23.5°$ (c 0.48, AcOH), Rf 0.48, Anal. for $C_{16}H_{24}N_2O_4$, Found C: 62.61, H: 7.86, N: 8.83; Calc'd. C: 62.31, H: 7.85, N: 9.09.

EXAMPLE 2

Step 1

11.0 g. of hydrochloride of (2RS,3R)-3-amino-2-hydroxy-4-phenylbutyronitrile is refluxed for 4 hours in 200 ml. of 6 N hydrochloric acid. Hydrochloric acid is distilled away under reduced pressure. 200 ml. of water is added and the reaction mixture is concentrated once more under reduced pressure. 100 ml. of water is added to the solid matter and the insoluble substance is filtered off, 100 ml. of acetone is added and the reaction mixture is adjusted to pH 5.5 with ammonia water and allowed to stand overnight in a refrigerator. The separated crystals are collected by filtration and rinsed with a water-/acetone (1:1) solution to prepare 6.19 g. of intended (2RS,3R)-AHPA.

Step 2

In the similar manner to Example 1; Step 2, (2RS,3R)-AHPA is benzyloxycarbonylated and resolved with brucine to prepare Z-(2S,3R)-AHPA. When the resulting Z-(2S,3R)-AHPA is allowed to react with an equimolar amount of HOSu and DCCD, Z-(2S,3R)-AHPA-OSu is obtained.

m.p. 111°–112° C., $[\alpha]_{578}^{25} +87.7°$ (c 0.52, AcOH), Anal. for $C_{22}H_{22}N_2O_7$, Found C: 61.27, H: 5.25, N: 6.47, Calc'd. C: 61.96, H: 5.20, N: 6.57.

Step 3

85 mg. of Z-(2S, 3R)-AHPA-OSu and 86 mg. of (S)-Leu-OBzl.TosOH are allowed to react for 12 hours in 5 ml. of dioxane at room temperature in the presence of 0.03 ml. of triethylamine. Then the reaction mixture is concentrated under reduced pressure. The residue is extracted with ethyl acetate and washed with 1 N sulfuric acid, water, 5% aqueous sodium bicarbonate solution and water in this order. Then the residue is dried over anhydrous magnesium sulfate and the solvent is distilled away to prepare a solid matter. When the solid matter is recrystallized from ethyl acetate-petroleum ether, 90 mg. of intended Z-(2S,3R)-AHPA-(S)-Leu-OBzl is obtained.

m.p. 122° C., $[\alpha]_{578}^{20}+15.1°$ (c 0.77, AcOH).

75 mg. of Z-(2S,3R)-AHPA-(S)-Leu-Obzl is then treated in a similar manner to Example 1, Step 4 to thereby prepare 33 mg. of (2S,3R)-3-amino-2-hydroxy-4-phenylbutanoyl-(S)-leucine.

$[\alpha]_{578}^{25}-21.8°$ (c 0.45, AcOH), Rf 0.48.

EXAMPLE 3

Step 1

330 mg. of Z-(2S,3R)-AHPA prepared in the similar manner to Example 1, Step 2, 162 mg. of HOBt, 217 mg. of the hydrochloride of (S)-Leu-OMe, 0.17 ml. of triethylamine and 206 mg. of DCCD are reacted in the similar manner to Example 1, Step 3 to prepare 293 mg. of Z-(2S,3R)-AHPA-(S)-Leu-OMe.

m.p. 120° C., $[\alpha]_{578}^{24}-22.1°$ (c 1.09, AcOH), Anal. for $C_{25}H_{32}N_2O_6$, Found C: 65.91, H: 7.16, N: 6.28; Calc'd. C: 65.77, H: 7.07, N: 6.14

Step 2

250 mg. of Z-(2S,3R)-AHPA-(S)-Leu-OMe is dissolved in 10 ml. of methanol and 0.6 ml. of 1 N aqueous sodium hydroxide solution is added to the solution and the resulting mixture is agitated for 6 hours at room temperature. Then methanol is distilled away under reduced pressure and water is added to the remaining liquor, which is then adjusted to pH 2 with 1 N sulfuric acid. The separated precipitates are extracted with ethyl acetate, washed with water, dehydrated to dryness over anhydrous magnesium sulfate and the solvent is removed. The resulting solid matter is crystallized from ethyl acetate-petroleum ether. When the crystal is recrystallized from the same solvents, 150 mg. of Z-(2S,3R)-AHPA-(S)-Leu is obtained.

m.p. 209° C. $[\alpha]_{578}^{31}+27.2°$ (c 0.71, AcOH), Anal. for $C_{24}H_{30}N_2O_6$, Found C: 65.29, H: 6.75, N: 6.33; Calc'd. C: 65.14, H: 6.75, N: 6.46

Step 3

120 mg. of Z-(2S,3R)-AHPA-(S)-Leu is dissolved in 30 ml. of methanol and hydrogenated for 3 hours with 50 mg. of palladium black. Then the catalyst is filtered off and methanol is distilled away to crystallize 54 mg. of (2S,3R)-3-amino-2-hydroxy-4-phenylbutanoyl-(S)-leucine from methanol-ethyl acetate.

$[\alpha]_{578}^{23}-22.7°$ (c 0.95, AcOH), Rf 0.48.

EXAMPLE 4

85 mg. of Z-(2S,3R)-AHPA-OSu prepared in the similar manner to Example 2, Step 2 is allowed to react with 54 mg. of (S)-Ley for 2 days at room temperature in 5 ml. of dioxane and 5 ml. of water in the presence of 0.03 ml. of triethylamine. The reaction mixture is concentrated under reduced pressure. 30 ml. of water is added to the residue and the solution is then adjusted to pH 2 with 1 N sulfuric acid and extraction is effected with 50 ml. of ethyl acetate. The ethyl acetate layer is washed with 1 N sulfuric acid, water, 5% aqueous sodium bicarbonate solution and water in this order and dehydrated to dryness with anhydrous magnesium sulfate. Ethyl acetate is removed and the resulting solid matter is crystallized from ethyl acetate-petroleum ether. When the crystal is reprecipitated from the same solvents, 63 mg. of intended Z-(2S,3R)-AHPA-(S)-Leu is obtained.

m.p. 209° C., $[\alpha]_{578}^{24}+26.7°$ (c 0.55, AcOH).

When 45 mg. of Z-(2S,3R)-AHPA-(S)-Leu is treated in the similar manner to Example 3, Step 3, 15 mg. of Bestatin is obtained.

$[\alpha]_{578}^{24}-22.3°$ (c 0.52, AcOH), Rf 0.48.

EXAMPLE 5

330 mg. of Z-(2S,3R)-AHPA prepared in the similar manner to Example 1, Step 2 is treated in the similar manner to Example 1, Step 3 with 472 mg. of (R)-Leu-OBzl.TosOH, 162 mg. of HOBt, 0.14 ml. of triethylamine and 206 mg. of DCCD to prepare 450 mg. of Z-(2S,3R)-AHPA-(R)-Leu-OBzl.

m.p. 118°–119° C., $[\alpha]_{578}^{23}+43.0°$ (c 1.23, AcOH).

When 430 mg. of resulting Z-(2S,3R)-AHPA-(R)-Leu-OBzl is treated in the similar manner to Example 1, Step 4, 144 mg. of (2S,3R)-3-amino-2-hydroxy-4-phenylbutanoyl-(S)-leucine is obtained.

$[\alpha]_{578}^{28}+0.9°$ (c 0.47, AcOH), Rf 0.49, Anal. for $C_{16}H_{24}N_2O_4$, Found C: 62.47; H: 7.89; N: 9.09; Calc'd. C: 62.31; H: 7.85; N: 9.09.

EXAMPLE 6

Step 1

Z-(2RS,3S)-AHPA is prepared by benzyloxycarbonylation of (2RS,3S)-AHPA which has been prepared in the similar manner to Example 1, Step 1. 7.75 g. of Z-(2RS,3S)-AHPA and 6.69 g. of dehydroabietylamine are allowed to react to prepare a diastereoisomer, which is then dissolved in ether so as to filter off the hardly soluble dehydroabietylamine salt of Z-(2R,3R)-AHPA. The filtered ether solution is concentrated under reduced pressure and the resultant oily material is treated with ethyl acetate-1 N hydrochloric acid to prepare crude Z-(2S,3S)-AHPA when the crystal is re-precipitated twice from ethyl acetate-petroleum ether, 2.16 g. of pure Z-(2S,3S)-AHPA is obtained.

m.p. 175°–176° C. $[\alpha]_{578}^{25}+5.6°$ (c 1.39, AcOH).

Step 2

660 mg. of Z-(2S,3S)-AHPA, 944 mg. of (S)-Leu-OBzl·TosOH, 324 mg. of HOBt, 0.34 ml. of triethylamine and 412 mg. of DCCD are treated in the similar manner to Example 1, Step 3 to prepare 710 mg. of Z-(2S,3S)-AHPA-(S)-Leu-OBzl.

m.p. 128° C. $[\alpha]_{578}^{25}-38.0°$ (c 0.81, AcOH).

500 mg. of Z-(2S,3S)-AHPA-(S)-Leu-OBzl is treated in the similar manner to Example 1, Step 4 to prepare 270 mg. of (2S,3S)-3-amino-2-hydroxy-4-phenylbutanoyl-(S)-leucine.

$[\alpha]_{578}^{24}-61.3°$ (c 0.56, AcOH), Rf 0.37, Anal. for $C_{16}H_{24}N_2O_4$, Found C: 61.99, H: 7.71, N: 9.13; Calc'd. C: 62.31, H: 7.85, N: 9.09.

EXAMPLE 7

165 mg. of Z-(2S,3S)-AHPA prepared in the similar manner to Example 6, Step 1, 237 mg. of (R)-Leu-OBzl·TosOH, 81 mg. of HOBt, 0.08 ml. of triethylamine and 103 mg. of DCCD are treated in the similar manner to Example 1, Step 3 to prepare 180 mg. of Z-(2S,3S)-AHPA-(R)-Leu-OBzl.

m.p. 128°–219° C., $[\alpha]_{578}^{23}$ −11.0° (c 1.02, AcOH).

155 mg. of Z-(2S,3S)-AHPA-(R)-Leu-OBzl is treated in the similar manner to Example 1, Step 4 to prepare 72.1 mg. of (2S,3S)-3-amino-2-hydroxy-4-phenylbutanoyl-(R)-leucine.

$[\alpha]_{578}^{28}$ −31.4° (c 0.47, AcOH), Rf 0.52, Anal. for $C_{16}H_{24}N_2O_4$, Found C: 62.07, H: 7.63, N: 8.80; Calc'd. C: 62.31, H: 7.85, N: 9.09.

EXAMPLE 8

330 mg. of Z-(2S,3R)-AHPA prepared in the similar manner to Example 1, Step 2, 405 mg. of Gly-OBzl·TosOH, 162 mg. of HOBt, 0.14 ml. of triethylamine and 206 mg. of DCCD are treated in the similar manner to Example 1, Step 3 to prepare oily Z-(2S,3R)-AHPA-Gly-OBzl. When examined by a thin layer chromatography, this oily product was proved to be pure.

When the oily product is treated in the similar manner to Example 1, Step 4, 117 mg. of (2S,3R)-3-amino-2-hydroxy-4-phenylbutanoyl-glycine is obtained.

$[\alpha]_{578}^{23}$ −7.4° (c 0.49, AcOH), Rf 0.26, Anal. for $C_{12}H_{16}O_4N_2 \cdot CH_3OH$, Found C: 54.33, H: 6.87, N: 9.69; Calc'd. C: 54.92, H: 7.09, N: 9.87.

EXAMPLE 9

330 mg. of Z-(2S,3R)-AHPA prepared in the similar manner to Example 1, Step 2, 440 mg. of the hydrochloride of (S)-Ser(Bzl)-ONb 162 mg. of HOBt, 0.14 ml. of triethylamine and 206 mg. of DCCD are treated in the similar manner to Example 1, Step 3 to prepare 540 mg. of Z-(2S,3R)-AHPA-(S)-Ser(Bzl)-ONb.

m.p. 121.5° C., $[\alpha]_{578}^{22}$ +17.7° (c 1.07, AcOH)

When 500 mg. of Z-(2S,3R)-AHPA(S)-Ser(Bzl)-ONb is treated in the similar manner to Example 1, Step 4, 147 mg. of (2S,3R)-3-amino-2-hydroxy-4-phenylbutanoyl-(S)-serine is obtained.

$[\alpha]_{578}^{26}$ −9.0° (c 0.50, AcOH), Rf 0.20, Anal. for $C_{13}H_{18}O_5N_2 \cdot H_2O$, Found C: 51.39, H: 6.74, N: 8.97; Calc'd. C: 51.99, H: 6.71, N: 9.33.

EXAMPLE 10

330 mg. of Z-(2S,3R)-AHPA prepared in the similar manner to Example 1, Step 2, 400 mg. of the hydrochloride of (S)-Gln-OBzl, 162 mg. of HOBt, 0.14 ml. of triethylamine and 206 mg. of DCCD are treated in the similar manner to Example 1, Step 3 to prepare 200 mg. of Z-(2S,3R)-AHPA-(S)-Gln-OBzl.

m.p. 155° C., $[\alpha]_{578}^{22}$ +62.3° (c 0.75, AcOH)

When 180 mg. of Z-(2S,3R)-AHPA-(S)-Gln-OBzl is treated in the similar manner to Example 1, Step 4, 61 mg. of (2S,3R)-3-amino-2-hydroxy-4-phenylbutanoyl-(S)-glutamine is obtained.

$[\alpha]_{578}^{23}$ −9.9° (c 0.37, AcOH), Rf 0.17, Anal. for $C_{15}H_{21}O_5N_3 \cdot 2H_2O$, Found C: 50.64, H: 6.32, N: 11.61; Calc'd. C: 50.13, H: 7.01, N: 11.69.

EXAMPLE 11

330 mg. of Z-(2S,3R)-AHPA prepared in the similar manner to Example 1, Step 2, 600 mg. of (S)-Glu(OBzl)-OBzl·TosOH, 162 mg. of HOBt, 0.14 ml. of triethylamine and 206 mg. of DCCD are treated in the similar manner to Example 1, Step 3 to prepare 605 mg. of Z-(2S,3R)-AHPA-(S)-Glu(OBzl)-OBzl.

m.p. 119°–120° C., $[\alpha]_{578}^{23}$ +28.6° (c 1.04, AcOH).

When 250 mg. of Z-(2S,3R)-AHPA-(S)-Glu(OBzl)-OBzl is treated in the similar manner to Example 1, Step 4, 166 mg. of (2S,3R)-3-amino-2-hydroxy-4-phenylbutanoyl-(S)-glutamic acid is obtained.

$[\alpha]_{578}^{23}$ −18.4° (c 0.51, AcOH), Rf 0.27, Anal. for $C_{15}H_{20}O_6N_2$, Found C: 55.20, H: 5.90, N: 8.20; Calc'd. C: 55.55, H: 6.22, N: 8.64.

EXAMPLE 12

330 mg. of Z-(2S,3R)-AHPA prepared in the similar manner to Example 1, Step 2, 455 mg. of (S)-Val-OBzl·TosOH, 162 mg. of HOBt, 0.14 ml. of triethylamine and 206 mg. of DCCD are treated in the similar manner to Example 1, Step 3 to prepare 397 mg. of Z-(2S,3R)-AHPA-(S)-Val-OBzl.

m.p. 96.5°–97° C., $[\alpha]_{578}^{23}$ +19.2° (c 0.99, AcOH).

When 376 mg. of Z-(2S,3R)-AHPA-(S)-Val-OBzl is treated in the similar manner to Example 1, Step 4, 104 mg. of (2S,3R)-3-amino-2-hydroxy-4-phenylbutanoyl-(S)-valine is obtained.

$[\alpha]_{578}^{26}$ −1.4° (c 0.55, AcOH), Rf 0.42, Anal. for $C_{15}H_{22}O_4N_2$, Found C: 60.98, H: 7.59, N: 9.28; Calc'd. C: 61.20, H: 7.53, N: 9.52.

EXAMPLE 13

330 mg. of Z-(2S,3R)-AHPA prepared in the similar manner to Example 1, Step 2, 455 mg. of (S)-Nva-OBzl·TosOH, 162 mg. of HOBt, 0.14 ml. of triethylamine and 206 mg. of DCCD are treated in the similar manner to Example 1, Step 3 to prepare 310 mg. of Z-(2S,3R)-AHPA-(S)-Nva-Obzl.

m.p. 114°–115° C., $[\alpha]_{578}^{24}$ +22.0° (c 0.49, AcOH).

When 250 mg. of Z-(2S,3R)-AHPA-(S)-Nva-OBzl is treated in the similar manner to Example 1, Step 4, 110 mg. of (2S,3R)-3-amino-2-hydroxy-4-phenylbutanoyl-(S)-norvaline is obtained.

$[\alpha]_{578}^{31}$ −14.5° (c 0.50, AcOH), Rf 0.41, Anal. for $C_{15}H_{22}O_4N_2$, Found C: 59.42, H: 7.58, N: 9.09; Calc'd. C: 59.33, H: 7.64, N: 9.23.

EXAMPLE 14

When (2S,3R)-AHPA is t-butoxycarbonylated in the usual manner by use of t-butyl S-4,6-dimethylpyrimidine-2-ylthiolcarbonate, DCHA salt of Boc-(2S,3)-AHPA is obtained.

m.p. 158°–159° C., $[\alpha]_{578}^{25}$ +51.9° (c 0.89, AcOH).

When DCHA is removed from 952 mg. of this product by treatment with 1 N sulfuric acid and ethyl acetate the oily Boc-(2S,3R)-AHPA is obtained. The oily material and 440 mg. of the hydrochloride of (S)-Met-OMe are suspended in 20 ml. of tetrahydrofuran and neutralized with 0.308 ml. of triethylamine. The resulting solution is cooled to −5° C. and after adding 412 mg. of DCCD, agitated for 4 hours at room temperature.

The deposited crystal is filtered off, the mother liquor is concentrated under reduced pressure and the residue is dissolved in 200 ml. of ethyl acetate, washed with 1 N sulfuric acid, water, 5% aqueous sodium bicarbonate solution and water in this order and dehydrated to dryness over anhydrous magnesium sulfate.

The residue obtained by concentrating the mother liquor under reduced pressure is dissolved in an ethyl acetate-benzene mixture (2:5) and introduced into a column chromatograph employing silica gel G (trade name for an adsorbent for use in column chromatography manufactured by Merck Inc.). The fraction containing the intended material is collected and the solvent is distilled away under reduced pressure to obtain a solid matter. When the solid matter is recrystallized from ether-petroleum ether, 380 mg. of Boc-(2S,3R)-AHPA-(S)-Met-OMe is obtained.

m.p. 118° C., $[\alpha]_{578}^{24}+51.4°$ (c 0.56, AcOH).

When 280 mg. of Boc-(2S,3R)-AHPA-(S)-Met-OMe is treated in the similar manner to Example 3, Step 2, 200 mg. of Boc-(2S,3R)-AHPA-(S)-Met) is obtained.

m.p. 116° C. (foaming, $[\alpha]_{578}^{22}+44.1°$ (c 0.54, AcOH).

0.2 ml. of thioglycolic acid and 50% aqueous trifluoroacetic acid solution are added to 150 mg. of Boc-(2S,3R)-AHPA-(S)-Met and the mixture is agitated for one hour at room temperature.

An oily material obtained by concentrating the mixture under reduced pressure is dissolved in water and adsorbed to a column (5 ml.) which is packed with Dowex 50X4 (H type) (trade name for an ion exchange resin manufactured and sold by Dow Chemical Co.). Then, adsorbed material is eluted with a 2 N aqueous ammonium hydroxide solution and evaporated to dryness to obtain a solid material. When the solid material is recrystallized in a water-acetone mixture (1:1), 87 mg. of (2S,3R)-3-amino-2-hydroxy-4-phenylbutanoyl-(S)-methionine is obtained.

$[\alpha]_{578}^{27}-20.4°$ (c 0.49, AcOH), Rf 0.37, Anal. for $C_{15}H_{22}O_4N_2S\cdot\frac{1}{2}H_2O$, Found C: 53.64, H: 6.47, N: 8.11; Calc'd. C: 53.67, H: 6.91, N: 8.35.

EXAMPLE 15

330 mg. of Z-(2S,3R)-AHPA prepared in the similar manner to Example 1, Step 2, 472 mg. of (S)-Ile-OBzl·TosOH, 162 mg. of HOBt, 0.14 ml. of triethylamine and 206 mg. of DCCD are treated in the similar manner to Example 1, Step 3, to prepare 466 mg. of Z-(2S,3R)-AHPA-(S)-Ile-OBzl.

m.p. 100°-101° C., $[\alpha]_{578}^{23}+23.6°$ (c 1.0, AcOH).

When 440 mg. of Z-(2S,3R)-AHPA-(S)-Ile-OBzl is treated in the similar manner to Example 1, Step 4, 191 mg. of (2S,3R)-3-amino-2-hydroxy-4-phenylbutanoyl-(S)-isoleucine is obtained.

$[\alpha]_{578}^{26}+6.4°$ (c 0.52, AcOH), Rf 0.48, Anal. for $C_{16}H_{24}O_4N_2$, Found C: 62.31, H: 7.70, N: 8.99; Calc'd. C: 62.31, H: 7.85, N: 9.09.

EXAMPLE 16

330 mg. of Z-(2S,3R)-AHPA prepared in the similar manner to Example 1, Step 2, 472 mg. of (S)-Nle-OBzl·TosOH, 162 mg. of HOBt, 0.14 ml. of triethylamine and 206 mg. of DCCD are treated in the similar manner to Example 1, Step 3 to prepare 437 mg. of Z-(2S,3R)-AHPA-(S)-Nle-OBzl.

m.p. 114°-115° C., $[\alpha]_{578}^{24}+23.3°$ (c 0.94, AcOH).

350 mg. of Z-(2S,3R)-AHPA-(S)-Nle-OBzl is treated in the similar manner to Example 1, Step 4, 160 mg. of (2S,3R)-3-amino-2-hydroxy-4-phenylbutanoyl-(S)-norleucine is obtained.

$[\alpha]_{578}^{31}-8.9°$ (c 0.70, AcOH), Rf 0.47, Anal. for $C_{16}H_{24}O_4N_2\cdot H_2O$, Found C: 58.95, H: 7.84, N: 8.60; Calc'd. C: 58.88, H: 8.03, N: 8.58.

EXAMPLE 17

330 mg. of Z-(2S,3R)-AHPA prepared in the similar manner to Example 1, Step 2, 505 mg. of (RS)-Aoc-OBzl·TosOH, 162 mg. of HOBt, 0.14 ml. of triethylamine and 206 mg. of DCCD are treated in the similar manner to Example 1, Step 3, 430 mg. of Z-(2S,3R)-AHPA-(RS)-Aoc-OBzl is obtained.

m.p. 90°-92° C. $[\alpha]_{578}^{23}+32.9°$ (c 0.94, AcOH).

When 250 mg. of Z-(2S,3R)-AHPA-(RS)-Aoc-OBzl is treated in the similar manner to Example 1, Step 4, 74 mg. of (2S,3R)-3-amino-2-hydroxy-4-phenylbutanoyl-(RS)-2-aminooctanoic acid is obtained.

$[\alpha]_{578}^{21}-34.9°$ (c 0.53, AcOH), Rf 0.58, Anal. for $C_{18}H_{28}O_4N_2$, Found C: 64.43, H: 8.18, N: 8.02, Calc'd. C: 64.26, H: 8.39, N: 8.33.

EXAMPLE 18

330 mg. of Z-(2S,3R)-AHPA prepared in the similar manner to Example 1, Step 2, 513 mg. of (S)-Phe-OBzl·TosOH, 162 mg. of HOBt, 0.14 ml. of triethylamine and 206 mg. of DCCD are treated in the similar manner to Example 1, Step 3 to prepare 378 mg. of Z-(2S,3R)-AHPA-(S)-Phe-OBzl.

m.p. 111°-112° C., $[\alpha]_{578}^{23}+39.6°$ (c 0.97, AcOH).

When 355 mg. of Z-(2S,3R)-AHPA-(S)-Phe-OBzl is treated in the similar manner to Example 1, Step 4, 108 mg. of (2S,3R)-3-amino-2-hydroxy-4-phenylbutanoyl-(S)-phenylalanine is obtained.

$[\alpha]_{578}^{23}+0.4°$ (c 0.46, AcOH), Rf 0.44, Anal. for $C_{19}H_{22}O_4N_2\cdot CH_3OH$, Found C: 63.58, H: 6.45, N: 7.57; Calc'd. C: 64.15, H: 7.00, N: 7.48.

EXAMPLE 19

When 9.00 g. of benzyloxycarbonyl-(2RS,3R)-3-amino-2-hydroxypropionitrile is treated in the similar manner to Example 1, Step 1, 3.16 g. of (2RS,3R)-Me-Ise is obtained.

$[\alpha]_{578}^{22}-0.6°$ (c 1.10 N HCl) Rf 0, Anal. for $C_4H_9NO_3$, Found C: 40.53, H: 7.51, N: 11.95; Calc'd. C: 40.33, H: 7.62, N: 11.76.

When 1.10 g. of oily Z-(2RS,3R)-Me-Ise prepared by benzyloxycarbonylation of (2RS,3R)-Me-Ise, 1.97 g. of (S)-Leu-OBzl·TosOH, 675 mg. of HOBt, 0.70 ml. of triethylamine and 948 mg. of DCCD are treated in the similar manner to Example 1, Step 3, oily Z-(2RS,3R)-Me-Ise-(S)-Leu-OBzl is obtained. This oily product is proved to be pure by thin-layer chromatography.

When this oily Z-(2RS,3R)-Me-Ise-(S)-Leu-OBzl is treated in the similar manner to Example 1, Step 4, 765 mg. of (2RS,3R)-3-amino-2-hydroxypropionyl-(S)-leucine is obtained.

$[\alpha]_{578}^{29}-28.7°$ (c 1.09, AcOH), Anal. for $C_{10}H_{20}N_2O_4$, Found C: 51.49, H: 8.42, N: 11.96; Calc'd. C: 51.70, H: 8.58, N: 12.06.

EXAMPLE 20

2.76 g. of oily Z-(2RS,3R)-3-amino-2-hydroxy-5-methylhexanonitrile is dissolved in 30 ml. of concentrated hydrochloric acid and 30 ml. of dioxane. After adding 2.16 g. of anisole, the solution is refluxed for 4 hours. Dioxane is distilled away under reduced pressure and the remaining hydrochloric acid solution is washed with ether. The water layer is concentrated under reduced pressures to dryness.

Water is added to the residue and adsorbed on a column packed with Dowex 50×4 (H type) ®. After washing with water, the adsorbed material is eluted with 4 N aqueous ammonium hydroxide solution. Then the eluted solution is concentrated under reduced pressure to dryness.

When a water-acetone (1:1) mixture is added to the residue and the resulting crystal is separated by filtration, 0.82 g. of intended (2RS,3R)-iso-Bu-Ise is obtained.

$[\alpha]_{578}^{22} -8.3°$ (c 1.0, AcOH), Rf 0.18.

1.32 g. of oily Z-(2RS,3R)-iso-Bu-Ise prepared by benzyloxycarbonylation of (2RS,3R)-iso-Bu-Ise obtained in the aforementioned process, 1.76 g. of (S)-Leu-Obzl·TosOH, 0.60 g. of HOBt, 0.63 ml. of triethylamine and 0.92 g. of DCCD are treated in the similar manner to Example 1, Step 3 to obtain oily Z-(2RS,3R)-iso-Bu-Ise-(S)-Leu-OBzl. When this oily product is treated in the similar manner to Example 1, Step 4, 0.37 g. of (2RS,3R)-30-amino-2-hydroxy-5-methylhexanoyl-(S)-leucine is obtained.

$[\alpha]_{578}^{22} -26.6°$ (c 1.0, AcOH), Rf 0.43 and 0.49, Anal. for $C_{13}H_{26}N_2O_4$, Found C: 57.01, H: 9.80, N: 10.14; Calc'd. C: 56.91, H: 9.55, N: 10.21.

EXAMPLE 21

When 3.00 g. of Z-(2RS,3R)-3-amino-2-hydroxy-3-phenylpropionitrile is treated in the similar manner to Example 1, Step 1, 0.80 g. of (2RS,3R)-Ph-Ise is obtained.

$[\alpha]_{578}^{25} +9.5°$ (c 1.0, N HCl), Rf 0.13 and 0.17, Anal. for $C_9H_{11}NO_3$, Found C: 59.18, H: 6.15, N: 7.67; Calc'd. C: 59.66, H: 6.12, N: 7.73.

250 mg. of Z-(2RS,3R)-Ph-Ise [m.p. 170°–171° C., $[\alpha]_{578}^{23} +18.5°$ (c 0.47, AcOH)] prepared by benzyloxycarbonylation of (2RS,3R)-Ph-Ise, 394 mg. of (S)-Leu-OBzl·TosOH, 130 mg. of HOBt, 0.14 ml. of triethylamine and 165 mg. of DCCD are treated in the similar manner of Example 1, Step 3 to prepare 285 mg. of Z-(2RS,3R)-Ph-Ise-(S)-Leu-OBzl.

m.p. 93–95° C., $[\alpha]_{578}^{23} -34.7°$ (c 0.49, AcOH).

When 200 mg. of Z-(2RS,3R)-Ph-Ise-(S)-Leu-OBzl is treated in the similar manner to Example 1, Step 4, 45 mg. of (2RS,3R)-3-amino-2-hydroxy-3-phenylpropionyl-(S)-leucine is obtained.

$[\alpha]_{578}^{25} -2.4°$ (c 0.33, AcOH), Anal. for $C_{15}H_{22}O_4N_2$, Found C: 60.92, H: 7.67, N: 9.46; Calc'd. C: 61.20, H: 7.53, N: 9.52.

EXAMPLE 22

When 10.3 g. of Z-(2RS,3RS)-3-amino-2-hydroxy-4-p-chlorophenyl-butylonitrile is treated in the similar manner to Example 1, Step 1, 3.10 g. of (2RS,3RS)-AHPA (p-Cl) is obtained.

Rf 0.25, Anal. for $C_{10}H_{12}NO_3Cl$, Found C: 52.11, H: 5.17, N: 5.99; Calc'd. C: 52.29, H: 5.27, N: 6.10.

1.81 g. of Z-(2RS,3RS)-AHPA (p-Cl) (m.p. 147° C.) prepared by benzyloxycarbonylation of (2RS,3RS)-AHPA(p-Cl), 2.37 g. of (S)-Leu-OBzl·TosOH, 810 mg. of HOBt, 0.84 ml. of triethylamine and 1.03 g. of DCCD are treated in the similar manner to Example 1, Step 3, 2.50 g. of Z-(2RS,3RS)-AHPA(p-Cl)-(S)-Leu-OBzl is obtained.

m.p. 122°–124° C., $[\alpha]_{578}^{27} -12.3°$ (c 3.18, AcOH).

When 1.50 g. of Z-(2RS,3RS)-AHPA(p-Cl)-(S)-Leu-OBzl is treated in the similar manner to Example 1, Step 4, 650 mg. of (2RS,3RS)-3-amino-2-hydroxy-4-p-chlorophenylbutanoyl-(S)-leucine is obtained.

$[\alpha]_{578}^{26} -11.3°$ (c 1.33, AcOH), Rf 0.42 and 0.52, Anal. for $C_{16}H_{23}N_2O_4Cl$, Found C: 55.88, H: 7.29, N: 8.11; Calc'd. C: 56.05, H: 6.76, N: 8.17.

EXAMPLE 23

When 10.3 g. of Z-(2RS,3RS)-3-amino-2-hydroxy-4-o-chlorophenyl-butylonitrile is treated in the similar manner to Example 1, Step 1, 4.82 g. of (2RS,3RS)-AHPA (o-Cl) is obtained.

Rf 0.25 and 0.29, Anal. for $C_{10}H_{12}NO_3Cl$, Found C: 52.01, H: 5.17, N: 5.91; Calc'd. C: 52.29, H: 5.27, N: 6.10.

726 mg. of Z-(2RS,3RS)-AHPA(o-Cl) (m.p. 136.5° C.) prepared by benzyloxycarbonylation of (2RS,3RS)-AHPA(o-Cl), 944 mg. of (S)-Leu-OBzl·TosOH, 324 mg. of HOBt, 0.34 ml. of triethylamine and 412 mg. of DCCD are treated in the similar manner to Example 1, Step 3, 747 mg. of Z-(2RS,3RS)-AHPA(o-Cl)-(S)-Leu-OBzl is obtained.

m.p. 129°–132° C., $[\alpha]_{578}^{22} -29.1°$ (c 1.02, AcOH).

When 640 mg. of Z-(2RS,3RS)-AHPA(o-Cl)-(S)-Leu-OBzl is treated in the similar manner to Example 1, Step 4 and 107 mg. of (2RS,3RS)-3-amino-2-hydroxy-4-o-chlorophenylbutanoyl-(S)-leucine is obtained.

$[\alpha]_{578}^{21} -20.8°$ (c 0.48, AcOH) Rf 0.46, Anal. for $C_{16}H_{23}N_2O_4Cl$, Found C: 56.21, H: 6.56, N: 7.90; Calc'd. C: 56.05, H: 6.76, N: 8.17.

EXAMPLE 24

When 11.2 g. of Z-(2RS,3RS)-3-amino-2-hydroxy-4-p-methylphenylbutyronitrile is treated in the similar manner to Example 1, Step 1, 3.41 g. of (2RS,3RS)-AHPA(p-Me) is obtained.

Rf 0.20, Anal. for $C_{11}H_{15}NO_3$, Found C: 62.94, H: 7.01, N: 6.79; Calc'd. C: 63.14, H: 7.23, N: 6.99.

1.57 g. of Z-(2RS,3RS)-AHPA(p-Me) (m.p. 166.5°–8° C.) prepared by benzyloxycarbonylation of (2RS,3RS)-AHPA(p-Me), 1.42 g. of (S)-Leu-OBzl·TosOH, 486 mg. of HOBt, 0.50 ml. of triethylamine and 618 mg. of DCCD are treated in the similar manner to Example 1, Step 3, oily Z-(2RS,3RS)-AHPA-(S)-Leu-Obzl is obtained.

When the oily product is treated in the similar manner to Example 1, Step 4, 497 mg. of (2RS,3RS)-3-amino-2-hydroxy-4-p-methylphenylbutanoyl-(S)-leucine is obtained.

Rf 0.58 and 0.53 $[\alpha]_{578}^{25} -7.2°$ (c 0.96 AcOH), Anal. for $C_{17}H_{26}N_2O_4$, Found C: 63.08, H: 8.23, N: 8.49; Calc'd. C: 63.33, H: 8.13, N: 8.69.

EXAMPLE 25

103 mg. of Bestatin is dissolved in 5 ml. of acetic acid and 5 ml. of ethanol and hydrogenated catalytically on platinum oxide for 14 hours.

The catalyst is filtered off and the filtrate is concentrated under reduced pressure to dryness.

When the residue is triturated with ethyl acetate and collected by filtration 61 mg. of (2S,3R)-3-amino-2-hydroxy-4-cyclohexylbutanoyl-(S)-leucine is obtained.

Rf 0.47 $[\alpha]_{578}^{22} -30.5°$ (c 0.67, AcOH), Anal. for $C_{16}H_{30}N_2O_4$, Found C: 62.12, H: 9.52, N: 8.81; Calc'd. C: 61.12, H: 9.62, N: 8.91.

EXAMPLE 26

300 mg. of Bestatin is suspended in 10 ml. of concentrated sulfuric acid and 0.3 ml. of fuming nitric acid at 0° C. Reaction is continued for one hour at the same temperature after the suspended materials disappear. The reaction mixture is poured into 100 ml. of water and adsorbed to a column packed with Dowex 50X4 (H type). Then adsorbed material is eluted with 2 N aqueous ammonium hydroxide solution and evaporated to dryness. The residue is dissolved in 10 ml. of water and filtered and then the filtrate is lyophilized to give 213 mg. of (2S,3R)-3-amino-2-hydroxy-4-p-nitrophenylbutanoyl-(S)-leucine.

$[\alpha]_{578}^{28} +5.2°$ (c 0.5, AcOH), Rf 0.58, Anal. for $C_{16}H_{23}N_3O_6$ Found C: 54.28, H: 6.58, N: 11.88; Calc'd. C: 54.38, H: 6.56, N: 11.89.

EXAMPLE 27

100 mg. of (2S,3R)-AHPA(p-$NO_2$)-(S)-Leu obtained in Example 26 is dissolved in 10 ml. of methanol and catalytically hydrogenated on palladium black for 5 hours. The catalyst is filtered and the filtrate is concentrated under reduced pressure. The residue is dissolved in 5 ml. of water and filtered and then the filtrate is lyophilized to give 81 mg. of (2S,3R 3-amino-2-hydroxy-4-p-aminophenylbutanoyl-(S)-leucine.

$[\alpha]_{578}^{28} -23.2°$ (c 0.5, AcOH), Rf 0.25, Anal. for $C_{16}H_{25}N_3O_4$ Found C: 59.01, H: 7.91, N: 12.81, Calc'd. C: 59.42, H: 7.79, N: 13.00.

EXAMPLE 28

Step 1

22.0 g. of oily Z-(2RS,3RS)-3-amino-2-hydroxy-4-p-methoxyphenylbutyronitrile was dissolved in a mixture of 200 ml. of concentrated hydrochloric acid and 200 ml. of dioxane. After adding 13.2 g. of anisole the reaction mixture was refluxed for 12 hours. Then the dioxane was distilled away under reduced pressure, the resulting solution of hydrochloric acid washed with ether and the water layer concentrated under reduced pressure and evaporated to dryness. Subsequently, 100 ml. of water was added to the residual substance and the insoluble substance was separated by filtration. After adding an equal quantity of acetone the mixture was adjusted to pH 5.5 with ammonia water. The mixture was allowed to stand in a refrigerator. The deposited crystals were separated by filtration to obtain 6.73 g. of intended (2RS,3RS)-AHPA(P-OH).

Step 2

2.11 g. of (2RS,3RS)-ANPA obtained in Step 1 was dissolved in 10 ml of 1 N sodium hydroxide solution. While vigorously agitating the solution under cooling with ice, 4.5 ml. of Z-Cl was added in three portions over a period of 30 minutes. Then the reaction mixture was vigorously agitated for 1 hour under cooling with ice and for 3 hours at room temperature. During the reaction the pH was adjusted to 8-9 with 1 N sodium hydroxide solution.

When the reaction had been completed, 6 N hydrochloric acid was added to adjust the reaction mixture to pH 2. As a result oily material separated which was then extracted twice with 100 ml. of ethyl acetate. The ethyl acetate layer was washed with water and dehydrated to dryness by the use of anhydrous magnesium sulfate. After separating magnesium sulfate by filtration the filtrate was concentrated under reduced pressure and the residue crystallized in ethyl acetate-petroleum ether to provide 3.64 g. of Z-(2RS,3RS)-AHPA(P-OZ). M.p. 138°-140° C.

Step 3

479 mg. of Z-(2RS,3RS)-AHPA(P-OZ) and 162 mg. of HOBt were dissolved in 10 ml. of tetrahydrofuran. After adding 472 mg. of Leu-OBzl.TosOH the mixture was neutralized with 0.168 ml. of triethylamine and cooled to −5° C. Then 206 mg. of DCCD was added and the reaction mixture was allowed to stand overnight for reaction. Tetrahydrofuran was distilled away under reduced pressure and 30 ml. of ethyl acetate was added. After filtering off the insoluble substances the filtrate was washed with 1 N sulfuric acid, water, 5% aqueous sodium bicarbonate solution and water in that order and then dehydrated to dryness with anhydrous magnesium sulfate. The residue obtained by concentrating the filtrate under reduced pressure was solidified in ethyl acetate-petroleum ether. Recrystallization from the same solvent gave 450 mg. of Z-(2RS,3RS)-AHPA(P-OZ)-(S)-Leu-OBzl. M.p. 98°-99° C., $[\alpha]_{578}^{18} -14.0°$ (c 0.58, AcOH).

Step 4

400 mg. of Z-(2RS,3RS)-AHPA(P-OZ)-(S)-Leu-OBzl was dissolved in 10 ml. of methanol and hydrogenated for 3 hours with about 10 mg. of palladium black. The catalyst was filtered off and the solvent was concentrated under reduced pressure. When a recrystallization operation was carried out with methanol-ethyl acetate, 219 mg. of (2RS,3RS)-3-amino-2-hydroxy-4-p-hydroxyphenylbutanoyl-(S)-leucine were obtained.

$[\alpha]_{578}^{30} -88°$ (c 0.90, AcOH), Rf 0.48 and 0.50, Anal. for $C_{16}H_{24}N_2O_5$, Found: C, 59.38; H, 7.25; N, 8.95. Calc'd.: C, 59.24; H, 7.46; N, 8.64.

EXAMPLE 29

When 30 g. of Z-(2RS,3R)-3-amino-2-hydroxy-4-p-hydroxyphenylbutyronitrile was treated in similar manner to Example 28, Step 1, 12.61 g. of (2RS,3R)-AHPA(p-OH) was obtained.

Rf 0.20 Anal. for $C_{10}H_{12}NO_4$, Found: C, 58.63; H, 5.99; N, 7.43. Calc'd.: C, 58.81; H, 5.92; N, 7.82.

When (2RS,3R)-AHPA(p-OH) was benzyloxycarbonylated using benzyl-S-4,6-dimethylpyrimidine-2-ylthiocarbonate, Z-AHPA(p-OH) was obtained as DCHA salt. 15.22 g. of that crude DCHA salt was crystallized from methanol, ethyl acetate and petroleum ether and 3.2 g. of optically impure Z-(2R,3R)-AHPA(p-OH) DCHA salt was obtained as a first crop.

When the mother liquor was evaporated to dryness and the residue precipitated three times from ethyl acetate and ether, 5.02 g. of optically pure Z-(2S,3R)-AHPA(p-OH)DCHA salt was obtained.

M.p. 121°-122° C., $[\alpha]_{578}^{20} +49.9°$ (c 0.87, AcOH). Anal. for $C_{30}H_{42}N_2O_6$, Found: C, 69.81; H, 8.35; N, 6.42. Calc'd.: C, 69.46; H, 8.16; N, 6.17.

After a treatment of Z-(2S,3R)-AHPA(p-OH) DCHA salt (1.05 g.) with ethyl acetate and dilute $H_2SO_4$, the obtained Z-(2S,3R)-AHPA(p-OH), 866 mg. of (S)-Leu-OBzl.TosOH, 405 mg. of HOBt, 0.308 ml. of triethylamine and 412 mg. of DCCD were treated in similar manner to Example 28, Step 3. Oily Z-(2S,3R)-AHPA(p-OH)-(S)-Leu-OBzl was obtained quantitatively.

When the obtained oily Z-(2S,3R)-AHPA(p-OH)-(S)-Leu-OBzl was treated in similar manner to Example 28, Step 4, 630 mg. of (2S,3R)-3-amino-2-hydroxy-4-p-hydroxyphenylbutanol-(S)-leucine was obtained.

$[\alpha]_{578}^{29} -19.9°$ (c, 1.19, AcOH), Rf 0.48, Anal. for $C_{16}H_{23}N_2O_5$, Found: C, 59.98; H, 7.42; N, 10.42. Calc'd.: C, 60.55; H, 7.30; N, 10.08.

| Biological Testing | |
|---|---|
| (Inhibitory Activity Against Aminopeptidase B) | |
| Compounds | $ID_{50}$ (mcg./ml.) |
| Example 28 | 0.10 |
| Example 29 | 0.007 |

| Biological Testing |  |
|---|---|
| (Inhibitory Activity Against Aminopeptidase B) |  |
| Compounds | ID$_{50}$ (mcg./ml.) |
| Bestatin [(2S,3R)-AHPA-(S)—Leu] | 0.10 |

As you will see from the table the compound of Example 28 has substantially the same inhibitory effects as Bestatin but the compound of Example 29 can attain the same effect in a far less amount, one-fourteenth of Bestatin. Gathering from these results, it is expected that the new compounds, especially the compound of Example 29 which is an optically active form of the compound of Example 28, can be an extremely useful physiologically active substance.

The compound of Example 28 was also tested for its humoral antibody formation to find its efficacy as an immunizing cancer inhibitor. As a result, it was found that the compound has an effect of increasing the number of humoral antibody cells to a considerable degree. The results suggest that the compound can serve as an excellent immunizing cancer inhibitor. For the humoral antibody formation of Bestatin per se see J. Antibiotics, 29(81), 857–859 (August, 1976).

The effect of (2RS,3RS)-3-amino-2-hydroxy-4-hydroxyphenylbutanoyl-(S)-leucine on humoral antibody formation to Sheep Red Blood Cell (SRBC) in mice was studied as follows.

Mice (dd/y female) were immunized by intravenous injection of 10$^8$ SRBC. Intraperitoneal injection of (2RS,3RS)-3-amino-2-hydroxy-4-hydroxyphenylbutanoyl-(S)-leucine was made soon afterwards.

Bestatin [(2S,3R)-3-amino-2-hydroxy-4-phenylbutanoyl-(S)-leucine] and (2RS,3RS)-3-amino-2-hydroxy-4-p-chlorophenylbutanoyl-(S)-leucine were used as control.

Four days thereafter the number of plaque forming cells in the spleen were enumerated by JERNE's hemolytic plaque technique [Jerne, N. K.; A. A. Nordin & C. Henry: "The Agar Plaque Technique for Recognizing Antibody-producing Cells" in cell-bound antibodies (Wistar Institute Press, Philadelphia, 1963), pp. 109–122].

The results are as listed in Table 3.

Table 3

Effect of (2RS,3RS)-3-amino-2-hydroxy-4-hydroxyphenyl-butanoyl-(S)—Leucine on Humoral Antibody Formation to SRBC in Mice

| Name of Compound | Dose | Antibody Forming Cells Number | Treated Group / Non-treated Group |
|---|---|---|---|
| — | — | 12,500 ± 19,050 | — |
| (2RS,3RS)-3-amino-2-hydroxy-4-hydroxyphenylbutanoyl-(S)—leucine | 1 mg. | 207,400 ± 8,025 | 1.66 |
|  | 100 mcg. | 261,000 ± 11,700 | 2.09 |
|  | 10 mcg. | 208,000 ± 17,180 | 1.66 |
|  | 1 mcg. | 175,800 ± 8,200 | 1.41 |
|  | 0.1 mcg. | 141,000 ± 5,700 | 1.13 |
| Bestatin | 1 mg. | 190,000 ± 7,100 | 1.52 |
|  | 10 mcg. | 136,250 ± 6,500 | 1.09 |
| (2RS,3RS)-3-amino-2-hydroxy-4-p-chlorophenylbutanoyl-(S)—leucine | 1 mg. | 208,750 ± 8,000 | 1.67 |
|  | 10 mcg. | 133,750 ± 5,600 | 1.07 |

The number of antibody forming cells in mice group given 10 mcg. of Bestatin or (2RS,3RS)-3-amino-2-hydroxy-4-p-chlorophenylbutanoyl-(S)-leucine was nearly equal to that of non-treated group.

On the other hand the number of antibody forming cells in mice given 10 mcg. of (2RS,3RS)-3-amino-2-hydroxy-4-hydroxyphenylbutanoyl-(S)-leucine was 1.66 times larger than that of the non-treated mice and even when given only 1 mcg. it showed 1.41 times.

As mentioned above (2RS,3RS)-3-amino-2-hydroxy-4-hydroxybutanoyl-(S)-leucine has the excellent effect of increasing the number of antibody forming cells and did not increase the weight of the spleen or the number of nonspecific antibody forming cells.

REFERENCE EXAMPLE 1

Synthesis of Nitrile From Aldehyde

A solution consisting of 20.8 g. of sodium hydrogen sulfite and 50 ml. of water is added to about 52.7 g. of oily Z-(R)-phenylalaninal and separated adduct is filtered off and washed with water and ether in this order to prepare 77 g. of crude 3-benzyloxycarbonylamino-2-hydroxy-4-phenylbutyronitrile. 68 g. of resulting adduct is suspended in 250 ml. of water and cooled to 10°–12° C. After adding 500 ml. of ether, a solution consisting of 13 g. of potassium cyanide and 100 ml. of water is added dropwise over 30 minutes.

Then the reaction mixture is allowed to react for 3 hours at room temperature and the water layer is discarded. The ether layer is washed with an aqueous solution of sodium chloride and dehydrated to dryness over anhydrous magnesium sulfate.

When magnesium sulfate is filtered off and ether is distilled away under reduced pressure, 49 g. of oily benzyloxycarbonyl-(2RS,3R)-3-amino-2-hydroxy-4-phenylbutyronitrile is obtained.

Other nitrile derivatives used in the present invention are prepared in the same manner.

We claim:

1. A compound having the formula

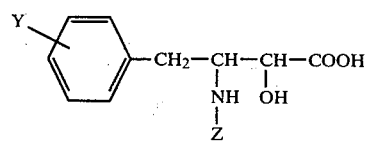

wherein Z is hydrogen or benzyloxycarbonyl and Y is benzyloxycarbonyloxy, hydroxy, chloro, methyl, nitro or amino.

2. A compound having the formula

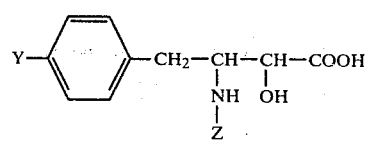

wherein Z is hydrogen or benzyloxycarbonyl and Y is benzyloxycarbonyloxy, hydroxy, chloro, methyl, nitro or amino.

3. A compound having the formula

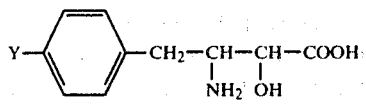

wherein Y is benzyloxycarbonyl, hydroxy, chloro, methyl, nitro or amino.

4. A compound having the formula

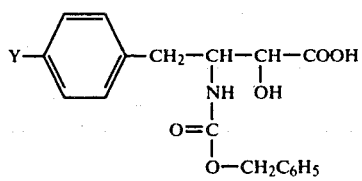

wherein Y is benzyloxycarbonyloxy, hydroxy, chloro, methyl, nitro or amino.

5. A compound having the formula

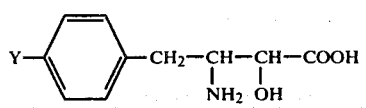

wherein Y is hydroxy, chloro or methyl.

6. A compound having the formula

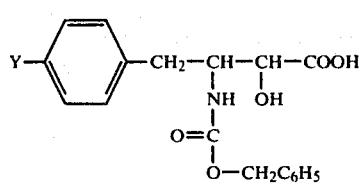

wherein Y is hydroxy, chloro or methyl.

7. A compound having the formula

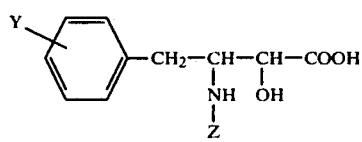

wherein Z is hydrogen or benzyloxycarbonyl and Y is benzyloxycarbonyloxy, hydroxy, chloro, methyl, nitro or amino and having the alpha carbon atom bearing the hydroxy group in the S configuration.

8. A compound having the formula

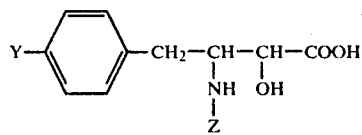

wherein Z is hydrogen or benzyloxycarbonyl and Y is benzyloxycarbonyloxy, hydroxy, chloro, methyl, nitro or amino and having the alpha carbon atom bearing the hydroxy group in the S configuration.

9. A compound having the formula

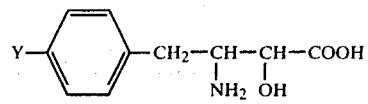

wherein Y is benzyloxycarbonyloxy, hydroxy, chloro, methyl, nitro or amino and having the alpha carbon atom bearing the hydroxy group in the S configuration.

10. A compound having the formula

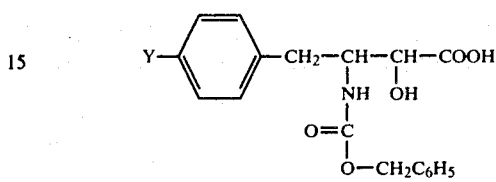

wherein Y is benxyloxycarbonyloxy, hydroxy, chloro, methyl, nitro or amino and having the alpha carbon atom bearing the hydroxy group in the S configuration.

11. A compound having the formula

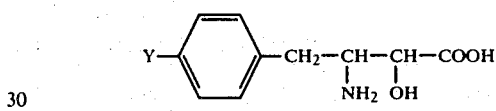

wherein Y is hydroxy, chloro or methyl and having the alpha carbon atom bearing the hydroxy group in the S configuration.

12. A compound having the formula

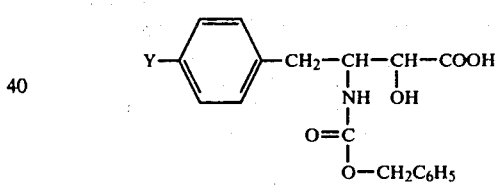

wherein Y is hydroxy, chloro or methyl and having the alpha carbon atom bearing the hydroxy group in the S configuration.

13. (2S,3R)-3-amino-2-hydroxy-4-p-hydroxyphenylbutanoic acid.

14. (2RS,3RS)-3-amino-2-hydroxy-4-phenylbutanoic acid.

15. (2RS,3RS)-3-amino-2-hydroxy-4-p-hydroxyphenylbutanoic acid.

16. (2RS,3RS)-3-amino-2-hydroxy-4-p-chlorophenylbutanoic acid.

17. (2RS,3RS)-3-amino-2-hydroxy-4-o-chlorophenylbutanoic acid.

18. (2RS,3RS)-3-amino-2-hydroxy-4-p-methylphenylbutanoic acid.

19. (2RS,3RS)-3-amino-2-hydroxy-4-p-benzyloxycarbonyloxyphenylbutanoic acid.

20. (2S,3R)-3-benzyloxycarbonylamino-2-hydroxy-4-phenylbutanoic acid.

21. (2S,4R)-3-benzyloxycarbonylamino-2-hydroxy-4-p-hydroxyphenylbutanoic acid.

22. (2RS,3RS)-3-benzyloxycarbonylamino-2-hydroxy-4-phenylbutanoic acid.

23. (2RS,3RS)-3-benzyloxycarbonylamino-2-hydroxy-4-p-hydroxyphenylbutanoic acid.
24. (2RS,3RS)-3-benzyloxycarbonylamino-2-hydroxy-4-p-chlorophenylbutanoic acid.
25. (2RS,3RS)-3-benzyloxycarbonylamino-2-hydroxy-4-o-chlorophenylbutanoic acid.
26. (2RS,3RS)-3-benzyloxycarbonylamino-2-hydroxy-4-p-methylphenylbutanoic acid.
27. (2RS,3RS)-3-benzyloxycarbonylamino-2-hydroxy-4-p-benzyloxycarbonyloxyphenylbutanoic acid.

* * * * *